United States Patent [19]

Sekiya et al.

[11] Patent Number: 5,063,247
[45] Date of Patent: Nov. 5, 1991

[54] DIPHENYLUREA DERIVATIVES

[75] Inventors: Tetsuo Sekiya, Yokohama; Shinya Inoue, Tokyo; Masao Taniguchi, Machida; Kohei Umezu, Yokohama; Kazuo Suzuki, Machida, all of Japan

[73] Assignee: Mitsubishi Kasei Corporation, Tokyo, Japan

[21] Appl. No.: 537,302

[22] Filed: Jun. 13, 1990

[30] Foreign Application Priority Data

Jun. 15, 1989 [JP] Japan .................................. 1-152594
Apr. 23, 1990 [JP] Japan .................................. 2-106986

[51] Int. Cl.$^5$ .................... A61K 31/17; C07C 335/18; C07C 275/34
[52] U.S. Cl. .................... 514/585; 514/587; 514/596; 514/598; 564/28; 564/29; 564/52; 564/53; 564/54
[58] Field of Search ........... 564/52, 53, 54, 28, 564/29; 514/596, 598, 585, 587

[56] References Cited

U.S. PATENT DOCUMENTS

| | | | |
|---|---|---|---|
| 3,579,578 | 5/1971 | Nikawitz et al. | 564/53 |
| 3,860,645 | 1/1975 | Nikawitz | 564/52 |
| 4,218,438 | 8/1980 | Callender et al. | 514/460 |
| 4,387,105 | 6/1983 | De Vries et al. | 564/52 |
| 4,405,644 | 9/1983 | Kabbe et al. | 564/54 |
| 5,003,106 | 3/1991 | De Vries | 564/53 |

FOREIGN PATENT DOCUMENTS

| | | | |
|---|---|---|---|
| 0049538 | 4/1982 | European Pat. Off. | 514/585 |
| 293880 | 12/1988 | European Pat. Off. | |
| 297610 | 1/1989 | European Pat. Off. | |
| 335374 | 10/1989 | European Pat. Off. | |
| 335375 | 10/1989 | European Pat. Off. | |
| 344425 | 12/1989 | European Pat. Off. | |
| 2070252 | 9/1971 | France | 564/53 |

OTHER PUBLICATIONS

Callender et al., "Anticoccidial Composition and Carbanilides", CA 94, 71498v (1981).

Primary Examiner—Richard L. Raymond
Assistant Examiner—Susan P. Treanor
Attorney, Agent, or Firm—Foley & Lardner

[57] ABSTRACT

Novel diphenylurea derivatives represented by the following formula (I):

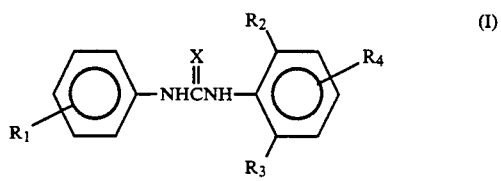

wherein $R_1$ is an alkyl group of 5 to 18 carbon atoms, each of $R_2$ and $R_3$ is independently an alkyl group of 1 to 5 carbon atoms, an alkoxy group of 1 to 5 carbon atoms or a halogen atom, $R_4$ is hydrogen atom, an alkyl group of 1 to 5 carbon atoms, an alkoxy group of 1 to 5 carbon atoms or a halogen atom, and X is oxygen atom or sulfur atom, are provided.

The compounds are potent in reducing the cholesterol level in serum, and useful for treating hyperlipemia and atherosclerosis.

5 Claims, No Drawings

DIPHENYLUREA DERIVATIVES

FIELD OF THE INVENTION

The present invention relates to diphenylurea derivatives which are potent in reducing a lipid level in blood and, therefore, useful as therapeutical medicines for hyperlipemia and atherosclerosis.

BACKGROUND OF THE INVENTION

Heretofore, it has be considered that metabolic error of lipids is one of the major dangerous factors causing an abnormal increase in and imbalance of a level of lipids in blood, which results in arteriosclerosis and finally, ischemic heart disease or cerebral embolism.

Some kinds of diphenylurea derivatives are known to exhibits an effect for reducing the lipid level in blood (German Offenlegungsschrift No. 2928485). However, these compounds are not sufficiently potent in reducing the level of cholesterol in blood as therapeutical medicines for hyperlipemia. Thus, it is further demanded to develop a more potent medicine which can reduce the level of cholesterol in blood.

SUMMARY OF THE INVENTION

As a result of the extensive studies, the present inventors have revealed that a specific class of diphenylurea derivatives is potent in reducing the level of cholesterol in blood and shows an inhibitory activity of an enzyme, acyl coenzyme cholesterol acyltransferase (ACAT) which was recently reported to act an important role at cholesterol metabolism, and achieved the present invention.

Specifically, the present invention provides a diphenylurea derivative represented by the following formula (I):

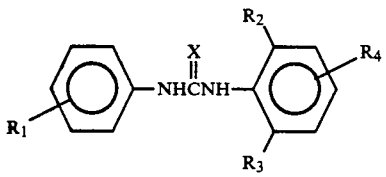

wherein $R_1$ is an alkyl group of 5 to 18 carbon atoms, each of $R_2$ and $R_3$ is independently an alkyl group of 1 to 5 carbon atoms, an alkoxy group of 1 to 5 carbon atoms or a halogen atom, $R_4$ is hydrogen atom, an alkyl group of 1 to 5 carbon atoms, an alkoxy group of 1 to 5 carbon atoms or a halogen atom, and X is oxygen atom or sulfur atom.

The compounds according to the invention are potent in reducing the cholesterol level in serum, and accordingly, useful for treating hyperlipemia and atherosclerosis.

DETAILED DESCRIPTION OF THE PREFERRED EMBODIMENTS

The diphenylurea derivative according to the present invention is represented by the above formula (I).

The examples of $R_1$ in the formula (I), i.e., an alkyl group of 5 to 18 carbon atoms, include n-pentyl group, neopentyl group, isopentyl group, n-hexyl group, isohexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, and n-octadecyl group. As the alkyl group of 1 to 5 carbon atoms of $R_2$, $R_3$ and $R_4$, there may be mentioned methyl group, ethyl group, n-propyl group, isopropyl group, n-butyl group, isobutyl group, t-butyl group, n-pentyl group, isopentyl group, sec-pentyl group, t-pentyl group, or neopentyl group. As the alkoxy group of 1 to 5 carbon atoms, there may be mentioned methoxy group, ethoxy group, n-propoxy group, isopropoxy group, n-butoxy group, isobutoxy group, t-butoxy group, n-pentyloxy group, isopentyloxy group, sec-pentyloxy group, t-pentyloxy group, or neopentyloxy group. Furthermore, as the halogen atom, there may be mentioned fluorine atom, chlorine atom, or bromine atom.

In the formula (I), $R_1$ may preferably be a normal alkyl group of 6 to 10 carbon atoms, and more preferably, $R_1$ is present at 2- or 4-position of the benzene ring, and more preferably, $R_4$ is hydrogen atom.

The preferred examples of the compounds according to the present invention include those listed in the following Table 1.

TABLE 1

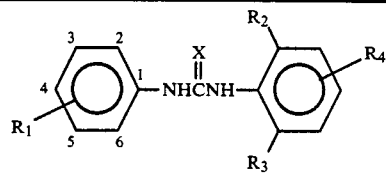

| $R_1$ | $R_2$ | $R_3$ | $R_4$ | X |
|---|---|---|---|---|
| 2-n-$C_5H_{11}$ | i-$C_3H_7$ | i-$C_3H_7$ | H | O |
| 2-n-$C_5H_{11}$ | Cl | Cl | H | O |
| 2-n-$C_5H_{11}$ | $CH_3$ | $CH_3$ | 4-$CH_3$ | O |
| 2-n-$C_6H_{13}$ | $C_2H_5$ | $C_2H_5$ | H | O |
| 2-n-$C_6H_{13}$ | i-$C_3H_7$ | i-$C_3H_7$ | H | O |
| 2-n-$C_6H_{13}$ | Cl | Cl | H | O |
| 2-n-$C_6H_{13}$ | $OCH_3$ | $OCH_3$ | H | O |
| 2-n-$C_6H_{13}$ | $CH_3$ | $CH_3$ | 4-$CH_3$ | O |
| 2-n-$C_7H_{15}$ | $C_2H_5$ | $C_2H_5$ | H | O |
| 2-n-$C_7H_{15}$ | i-$C_3H_7$ | i-$C_3H_7$ | H | O |
| 2-n-$C_7H_{15}$ | F | F | H | O |
| 2-n-$C_7H_{15}$ | Cl | Cl | H | O |
| 2-n-$C_7H_{15}$ | $OCH_3$ | $OCH_3$ | H | O |
| 2-n-$C_7H_{15}$ | t-$C_4H_9$ | $CH_3$ | H | O |
| 2-n-$C_7H_{15}$ | sec-$C_4H_9$ | $C_2H_5$ | H | O |
| 2-n-$C_7H_{15}$ | $CH_3$ | $CH_3$ | 4-$CH_3$ | O |
| 2-n-$C_7H_{15}$ | F | F | 4-F | O |
| 2-n-$C_7H_{15}$ | Cl | Cl | 4-Cl | O |
| 2-n-$C_7H_{15}$ | $OCH_3$ | $OCH_3$ | 4-$OCH_3$ | O |
| 2-n-$C_8H_{17}$ | $CH_3$ | $CH_3$ | H | O |
| 2-n-$C_8H_{17}$ | $C_2H_5$ | $C_2H_5$ | H | O |
| 2-n-$C_8H_{17}$ | i-$C_3H_7$ | i-$C_3H_7$ | H | O |
| 2-n-$C_8H_{17}$ | F | F | H | O |
| 2-n-$C_8H_{17}$ | Cl | Cl | H | O |
| 2-n-$C_8H_{17}$ | Br | Br | H | O |
| 2-n-$C_8H_{17}$ | $OCH_3$ | $OCH_3$ | H | O |
| 2-n-$C_8H_{17}$ | t-$C_4H_9$ | $CH_3$ | H | O |
| 2-n-$C_8H_{17}$ | s-$C_4H_9$ | $C_2H_5$ | H | O |
| 2-n-$C_8H_{17}$ | $CH_3$ | $CH_3$ | 4-$CH_3$ | O |
| 2-n-$C_8H_{17}$ | F | F | 4-F | O |
| 2-n-$C_8H_{17}$ | Cl | Cl | 3-Cl | O |
| 2-n-$C_8H_{17}$ | Cl | Cl | 4-Cl | O |
| 2-n-$C_8H_{17}$ | $OCH_3$ | $OCH_3$ | 4-$OCH_3$ | O |
| 2-n-$C_8H_{17}$ | Cl | Cl | 3-$CH_3$ | O |
| 2-n-$C_8H_{17}$ | Cl | Cl | 3-$OCH_3$ | O |
| 2-n-$C_9H_{19}$ | $C_2H_5$ | $C_2H_5$ | H | O |
| 2-n-$C_9H_{19}$ | i-$C_3H_7$ | i-$C_3H_7$ | H | O |
| 2-n-$C_9H_{19}$ | F | F | H | O |
| 2-n-$C_9H_{19}$ | Cl | Cl | H | O |
| 2-n-$C_9H_{19}$ | $OCH_3$ | $OCH_3$ | H | O |
| 2-n-$C_9H_{19}$ | $C_2H_5$ | $CH_3$ | H | O |
| 2-n-$C_9H_{19}$ | sec-$C_4H_9$ | $C_2H_5$ | H | O |
| 2-n-$C_9H_{19}$ | $CH_3$ | $CH_3$ | 4-$CH_3$ | O |
| 2-n-$C_9H_{19}$ | F | F | 4-F | O |
| 2-n-$C_9H_{19}$ | Cl | Cl | 4-Cl | O |

TABLE 1-continued

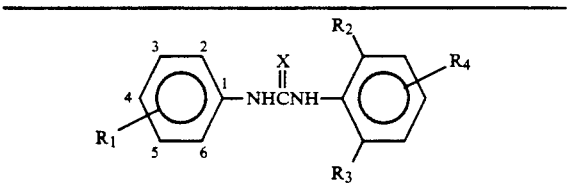

| $R_1$ | $R_2$ | $R_3$ | $R_4$ | X |
|---|---|---|---|---|
| 2-n-$C_9H_{19}$ | $OCH_3$ | $OCH_3$ | 4-$OCH_3$ | O |
| 2-n-$C_{10}H_{21}$ | $C_2H_5$ | $C_2H_5$ | H | O |
| 2-n-$C_{10}H_{21}$ | i-$C_3H_7$ | i-$C_3H_7$ | H | O |
| 2-n-$C_{10}H_{21}$ | Cl | Cl | H | O |
| 2-n-$C_{10}H_{21}$ | $CH_3$ | $CH_3$ | 4-$CH_3$ | O |
| 2-n-$C_{11}H_{23}$ | i-$C_3H_7$ | i-$C_3H_7$ | H | O |
| 2-n-$C_{11}H_{23}$ | Cl | Cl | H | O |
| 2-n-$C_{11}H_{23}$ | $CH_3$ | $CH_3$ | 4-$CH_3$ | O |
| 2-n-$C_{12}H_{25}$ | i-$C_3H_7$ | i-$C_3H_7$ | H | O |
| 2-n-$C_{12}H_{25}$ | Cl | Cl | H | O |
| 2-n-$C_{12}H_{25}$ | $CH_3$ | $CH_3$ | 4-$CH_3$ | O |
| 2-n-$C_{13}H_{27}$ | i-$C_3H_7$ | i-$C_3H_7$ | H | O |
| 2-n-$C_{13}H_{27}$ | Cl | Cl | H | O |
| 2-n-$C_{13}H_{27}$ | $CH_3$ | $CH_3$ | 4-$CH_3$ | O |
| 2-n-$C_{14}H_{29}$ | i-$C_3H_7$ | i-$C_3H_7$ | H | O |
| 2-n-$C_{14}H_{29}$ | Cl | Cl | H | O |
| 2-n-$C_{14}H_{29}$ | $CH_3$ | $CH_3$ | 4-$CH_3$ | O |
| 2-n-$C_{15}H_{31}$ | i-$C_3H_7$ | i-$C_3H_7$ | H | O |
| 2-n-$C_{15}H_{31}$ | Cl | Cl | H | O |
| 2-n-$C_{15}H_{31}$ | $CH_3$ | $CH_3$ | 4-$CH_3$ | O |
| 2-n-$C_{16}H_{33}$ | i-$C_3H_7$ | i-$C_3H_7$ | H | O |
| 2-n-$C_{16}H_{33}$ | Cl | Cl | H | O |
| 2-n-$C_{16}H_{33}$ | $CH_3$ | $CH_3$ | 4-$CH_3$ | O |
| 2-n-$C_{17}H_{35}$ | i-$C_3H_7$ | i-$C_3H_7$ | H | O |
| 2-n-$C_{17}H_{35}$ | Cl | Cl | H | O |
| 2-n-$C_{17}H_{35}$ | $CH_3$ | $CH_3$ | 4-$CH_3$ | O |
| 2-n-$C_{18}H_{37}$ | i-$C_3H_7$ | i-$C_3H_7$ | H | O |
| 2-n-$C_{18}H_{37}$ | Cl | Cl | H | O |
| 2-n-$C_{18}H_{37}$ | $CH_3$ | $CH_3$ | 4-$CH_3$ | O |
| 3-n-$C_5H_{11}$ | i-$C_3H_7$ | i-$C_3H_7$ | H | O |
| 3-n-$C_6H_{13}$ | i-$C_3H_7$ | i-$C_3H_7$ | H | O |
| 3-n-$C_7H_{15}$ | i-$C_3H_7$ | i-$C_3H_7$ | H | O |
| 3-n-$C_8H_{17}$ | i-$C_3H_7$ | i-$C_3H_7$ | H | O |
| 3-n-$C_9H_{19}$ | i-$C_3H_7$ | i-$C_3H_7$ | H | O |
| 3-n-$C_{10}H_{21}$ | i-$C_3H_7$ | i-$C_3H_7$ | H | O |
| 3-n-$C_{11}H_{23}$ | i-$C_3H_7$ | i-$C_3H_7$ | H | O |
| 3-n-$C_{12}H_{25}$ | i-$C_3H_7$ | i-$C_3H_7$ | H | O |
| 3-n-$C_{13}H_{27}$ | i-$C_3H_7$ | i-$C_3H_7$ | H | O |
| 3-n-$C_{14}H_{29}$ | i-$C_3H_7$ | i-$C_3H_7$ | H | O |
| 3-n-$C_{15}H_{31}$ | i-$C_3H_7$ | i-$C_3H_7$ | H | O |
| 3-n-$C_{16}H_{33}$ | i-$C_3H_7$ | i-$C_3H_7$ | H | O |
| 3-n-$C_{17}H_{35}$ | i-$C_3H_7$ | i-$C_3H_7$ | H | O |
| 3-n-$C_{18}H_{37}$ | i-$C_3H_7$ | i-$C_3H_7$ | H | O |
| 4-n-$C_5H_{11}$ | i-$C_3H_7$ | i-$C_3H_7$ | H | O |
| 4-n-$C_5H_{11}$ | Cl | Cl | H | O |
| 4-n-$C_5H_{11}$ | $CH_3$ | $CH_3$ | 4-$CH_3$ | O |
| 4-n-$C_6H_{13}$ | $C_2H_5$ | $C_2H_5$ | H | O |
| 4-n-$C_6H_{13}$ | i-$C_3H_7$ | i-$C_3H_7$ | H | O |
| 4-n-$C_6H_{13}$ | Cl | Cl | H | O |
| 4-n-$C_6H_{13}$ | $OCH_3$ | $OCH_3$ | H | O |
| 4-n-$C_6H_{13}$ | $CH_3$ | $CH_3$ | 4-$CH_3$ | O |
| 4-n-$C_7H_{15}$ | $C_2H_5$ | $C_2H_5$ | H | O |
| 4-n-$C_7H_{15}$ | i-$C_3H_7$ | i-$C_3H_7$ | H | O |
| 4-n-$C_7H_{15}$ | F | F | H | O |
| 4-n-$C_7H_{15}$ | Cl | Cl | H | O |
| 4-n-$C_7H_{15}$ | $OCH_3$ | $OCH_3$ | H | O |
| 4-n-$C_7H_{15}$ | t-$C_4H_9$ | $CH_3$ | H | O |
| 4-n-$C_7H_{15}$ | sec-$C_4H_9$ | $C_2H_5$ | H | O |
| 4-n-$C_7H_{15}$ | $CH_3$ | $CH_3$ | 4-$CH_3$ | O |
| 4-n-$C_7H_{15}$ | F | F | 4-F | O |
| 4-n-$C_7H_{15}$ | Cl | Cl | 4-Cl | O |
| 4-n-$C_7H_{15}$ | $OCH_3$ | $OCH_3$ | 4-$OCH_3$ | O |
| 4-n-$C_8H_{17}$ | $CH_3$ | $CH_3$ | H | O |
| 4-n-$C_8H_{17}$ | $C_2H_5$ | $C_2H_5$ | H | O |
| 4-n-$C_8H_{17}$ | i-$C_3H_7$ | i-$C_3H_7$ | H | O |
| 4-n-$C_8H_{17}$ | F | F | H | O |
| 4-n-$C_8H_{17}$ | Cl | Cl | H | O |
| 4-n-$C_8H_{17}$ | Br | Br | H | O |
| 4-n-$C_8H_{17}$ | $OCH_3$ | $OCH_3$ | H | O |
| 4-n-$C_8H_{17}$ | t-$C_4H_9$ | $CH_3$ | H | O |
| 4-n-$C_8H_{17}$ | s-$C_4H_9$ | $C_2H_5$ | H | O |
| 4-n-$C_8H_{17}$ | $CH_3$ | $CH_3$ | 4-$CH_3$ | O |
| 4-n-$C_8H_{17}$ | F | F | 4-F | O |
| 4-n-$C_8H_{17}$ | Cl | Cl | 3-Cl | O |
| 4-n-$C_8H_{17}$ | Cl | Cl | 4-Cl | O |
| 4-n-$C_8H_{17}$ | $OCH_3$ | $OCH_3$ | 4-$OCH_3$ | O |
| 4-n-$C_8H_{17}$ | Cl | Cl | 3-$CH_3$ | O |
| 4-n-$C_8H_{17}$ | Cl | Cl | 3-$OCH_3$ | O |
| 4-n-$C_9H_{19}$ | $C_2H_5$ | $C_2H_5$ | H | O |
| 4-n-$C_9H_{19}$ | i-$C_3H_7$ | i-$C_3H_7$ | H | O |
| 4-n-$C_9H_{19}$ | F | F | H | O |
| 4-n-$C_9H_{19}$ | Cl | Cl | H | O |
| 4-n-$C_9H_{19}$ | $OCH_3$ | $OCH_3$ | H | O |
| 4-n-$C_9H_{19}$ | $C_2H_5$ | $CH_3$ | H | O |
| 4-n-$C_9H_{19}$ | sec-$C_4H_9$ | $C_2H_5$ | H | O |
| 4-n-$C_9H_{19}$ | $CH_3$ | $CH_3$ | 4-$CH_3$ | O |
| 4-n-$C_9H_{19}$ | F | F | 4-F | O |
| 4-n-$C_9H_{19}$ | Cl | Cl | 4-Cl | O |
| 4-n-$C_9H_{19}$ | $OCH_3$ | $OCH_3$ | 4-$OCH_3$ | O |
| 4-n-$C_{10}H_{21}$ | $C_2H_5$ | $C_2H_5$ | H | O |
| 4-n-$C_{10}H_{21}$ | i-$C_3H_7$ | i-$C_3H_7$ | H | O |
| 4-n-$C_{10}H_{21}$ | Cl | Cl | H | O |
| 4-n-$C_{10}H_{21}$ | $CH_3$ | $CH_3$ | 4-$CH_3$ | O |
| 4-n-$C_{11}H_{23}$ | i-$C_3H_7$ | i-$C_3H_7$ | H | O |
| 4-n-$C_{11}H_{23}$ | Cl | Cl | H | O |
| 4-n-$C_{11}H_{23}$ | $CH_3$ | $CH_3$ | 4-$CH_3$ | O |
| 4-n-$C_{12}H_{25}$ | i-$C_3H_7$ | i-$C_3H_7$ | H | O |
| 4-n-$C_{12}H_{25}$ | Cl | Cl | H | O |
| 4-n-$C_{12}H_{25}$ | $CH_3$ | $CH_3$ | 4-$CH_3$ | O |
| 4-n-$C_{13}H_{27}$ | i-$C_3H_7$ | i-$C_3H_7$ | H | O |
| 4-n-$C_{13}H_{27}$ | Cl | Cl | H | O |
| 4-n-$C_{13}H_{27}$ | $CH_3$ | $CH_3$ | 4-$CH_3$ | O |
| 4-n-$C_{14}H_{29}$ | i-$C_3H_7$ | i-$C_3H_7$ | H | O |
| 4-n-$C_{14}H_{29}$ | Cl | Cl | H | O |
| 4-n-$C_{14}H_{29}$ | $CH_3$ | $CH_3$ | 4-$CH_3$ | O |
| 4-n-$C_{15}H_{31}$ | i-$C_3H_7$ | i-$C_3H_7$ | H | O |
| 4-n-$C_{15}H_{31}$ | Cl | Cl | H | O |
| 4-n-$C_{15}H_{31}$ | $CH_3$ | $CH_3$ | 4-$CH_3$ | O |
| 4-n-$C_{16}H_{33}$ | i-$C_3H_7$ | i-$C_3H_7$ | H | O |
| 4-n-$C_{16}H_{33}$ | Cl | Cl | H | O |
| 4-n-$C_{16}H_{33}$ | $CH_3$ | $CH_3$ | 4-$CH_3$ | O |
| 4-n-$C_{17}H_{35}$ | i-$C_3H_7$ | i-$C_3H_7$ | H | O |
| 4-n-$C_{17}H_{35}$ | Cl | Cl | H | O |
| 4-n-$C_{17}H_{35}$ | $CH_3$ | $CH_3$ | 4-$CH_3$ | O |
| 4-n-$C_{18}H_{37}$ | i-$C_3H_7$ | i-$C_3H_7$ | H | O |
| 4-n-$C_{18}H_{37}$ | Cl | Cl | H | O |
| 4-n-$C_{18}H_{37}$ | $CH_3$ | $CH_3$ | 4-$CH_3$ | O |

The above examples are those wherein X in the formula (I) is oxygen atom. The compounds of the present invention also include those wherein X is sulfur atom. The examples are shown in the following Table 2.

TABLE 2

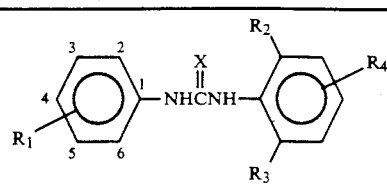

| $R_1$ | $R_2$ | $R_3$ | $R_4$ | X |
|---|---|---|---|---|
| 2-n-$C_6H_{13}$ | i-$C_3H_7$ | i-$C_3H_7$ | H | S |
| 2-n-$C_7H_{15}$ | i-$C_3H_7$ | i-$C_3H_7$ | H | S |
| 2-n-$C_8H_{17}$ | i-$C_3H_7$ | i-$C_3H_7$ | H | S |
| 2-n-$C_9H_{19}$ | i-$C_3H_7$ | i-$C_3H_7$ | H | S |
| 2-n-$C_{10}H_{21}$ | i-$C_3H_7$ | i-$C_3H_7$ | H | S |
| 3-n-$C_6H_{13}$ | i-$C_3H_7$ | i-$C_3H_7$ | H | S |
| 3-n-$C_7H_{15}$ | i-$C_3H_7$ | i-$C_3H_7$ | H | S |

TABLE 2-continued

[Structure: phenyl-NHC(X)NH-phenyl with R1 on left ring (positions 3,4,5), R2,R3,R4 on right ring]

| R1 | R2 | R3 | R4 | X |
|---|---|---|---|---|
| 3-n-$C_8H_{17}$ | i-$C_3H_7$ | i-$C_3H_7$ | H | S |
| 3-n-$C_9H_{19}$ | i-$C_3H_7$ | i-$C_3H_7$ | H | S |
| 3-n-$C_{10}H_{21}$ | i-$C_3H_7$ | i-$C_3H_7$ | H | S |
| 4-n-$C_5H_{11}$ | i-$C_3H_7$ | i-$C_3H_7$ | H | S |
| 4-n-$C_6H_{13}$ | i-$C_3H_7$ | i-$C_3H_7$ | H | S |
| 4-n-$C_6H_{13}$ | Cl | Cl | 3-$CH_3$ | S |
| 4-n-$C_7H_{15}$ | i-$C_3H_7$ | i-$C_3H_7$ | H | S |
| 4-n-$C_7H_{15}$ | Cl | Cl | 4-Cl | S |
| 4-n-$C_8H_{17}$ | $C_2H_5$ | $C_2H_5$ | H | S |
| 4-n-$C_8H_{17}$ | i-$C_3H_7$ | i-$C_3H_7$ | H | S |
| 4-n-$C_8H_{17}$ | $OCH_3$ | $OCH_3$ | H | S |
| 4-n-$C_8H_{17}$ | Cl | Cl | H | S |
| 4-n-$C_9H_{19}$ | i-$C_3H_7$ | i-$C_3H_7$ | H | S |
| 4-n-$C_9H_{19}$ | $OCH_3$ | $OCH_3$ | 4-$OCH_3$ | S |
| 4-n-$C_{10}H_{21}$ | i-$C_3H_7$ | i-$C_3H_7$ | H | S |
| 4-n-$C_{11}H_{23}$ | i-$C_3H_7$ | i-$C_3H_7$ | H | S |
| 4-n-$C_{12}H_{25}$ | i-$C_3H_7$ | i-$C_3H_7$ | H | S |
| 4-n-$C_{13}H_{27}$ | i-$C_3H_7$ | i-$C_3H_7$ | H | S |
| 4-n-$C_{14}H_{29}$ | i-$C_3H_7$ | i-$C_3H_7$ | H | S |
| 4-n-$C_{15}H_{31}$ | i-$C_3H_7$ | i-$C_3H_7$ | H | S |
| 4-n-$C_{16}H_{33}$ | i-$C_3H_7$ | i-$C_3H_7$ | H | S |
| 4-n-$C_{17}H_{35}$ | i-$C_3H_7$ | i-$C_3H_7$ | H | S |
| 4-n-$C_{18}H_{37}$ | i-$C_3H_7$ | i-$C_3H_7$ | H | S |

It should be, however, understood that the present invention is not limited to the above examples.

The compounds of the present invention may be prepared, for example, according to the processes described below.

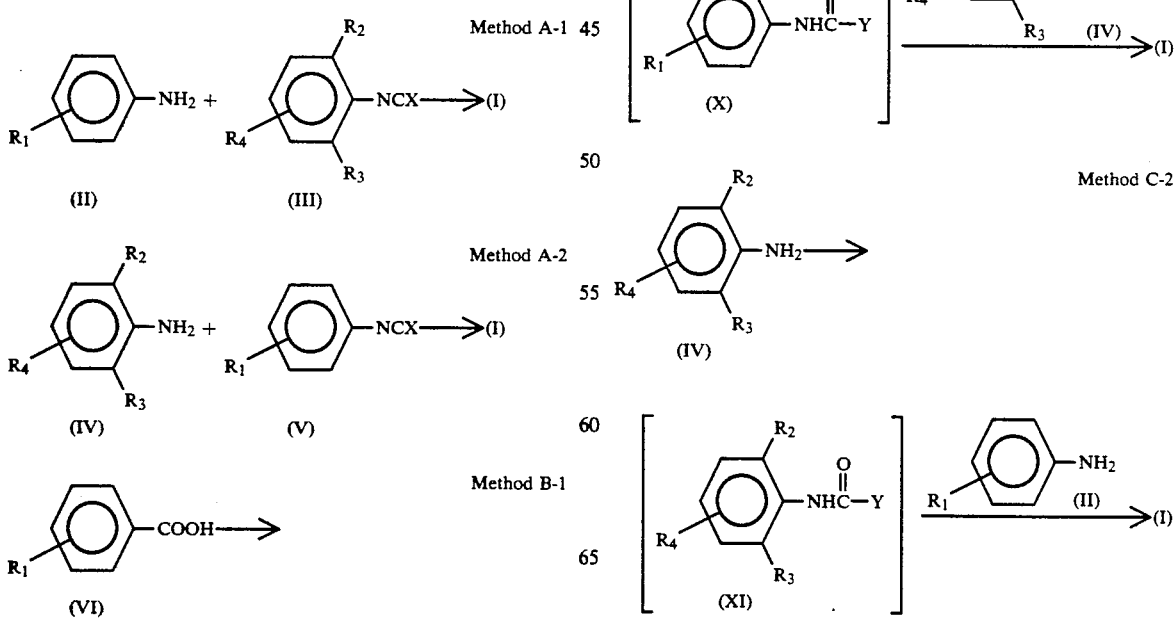

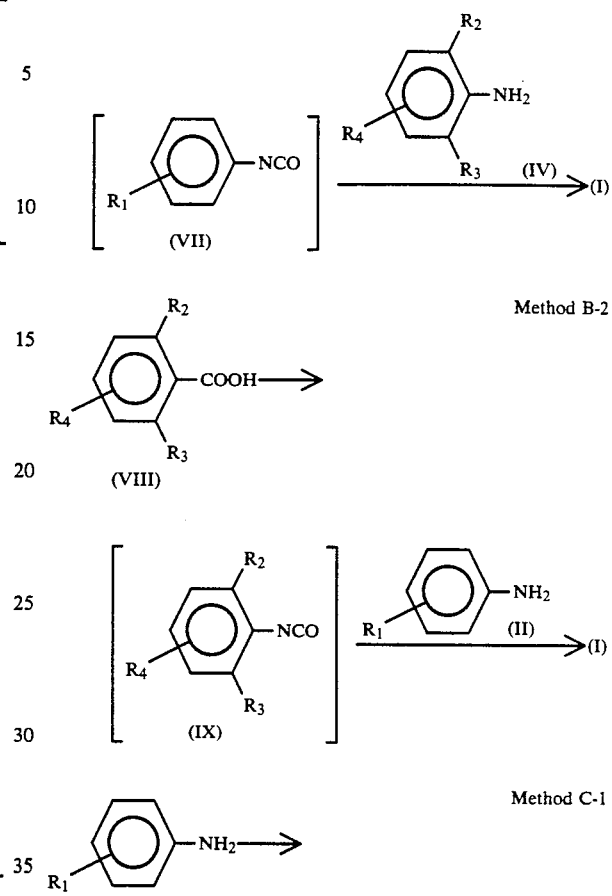

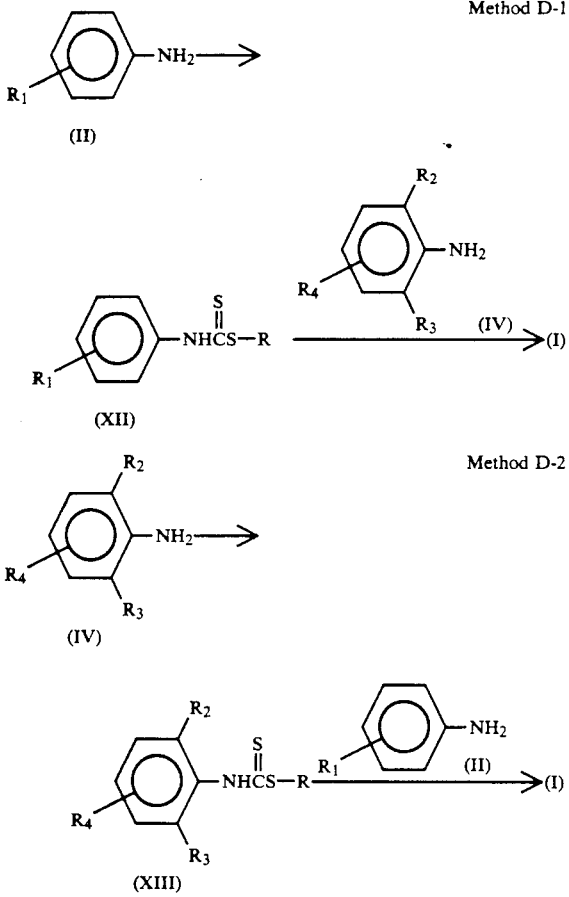

wherein $R_1$, $R_2$, $R_3$, $R_4$ and X are the same as defined above, Y is a leaving group such as chlorine atom or aryloxy group, and R is an alkyl group of 1 to 3 carbon atoms.

According to Method A-1, the compound (I) of the invention is prepared by reacting an aniline derivative of general formula (II) with a phenyl isocyanate or phenyl isothiocyanate derivative of the formula (III) at a temperature range of 0° C. to ca. 150° C. in an inert solvent such as benzene, toluene, xylene, hexane, heptane, tetrahydrofuran (THF), dioxane, ether, or N,N-dimethylformamide. Method A-2 comprises the preparation of the compound (I) of the invention by reacting an aniline derivative of formula (IV) with a phenyl isocyanate or phenyl isothiocyanate of the formula (V) in a similar manner to Method A-1.

According to Method B-1, the compound (I) of the invention wherein X is oxygen is prepared by converting a benzoic acid derivative of the formula (VI) into a phenyl isocyanate derivative of the formula (VII) using different procedures, followed by reacting an aniline derivative of the formula (IV) with the resulting isocyanate at a temperature range of 0° C. to ca. 150° C. The conversion of the benzoic acid derivative of the formula (VI) into the phenyl isocyanate derivative of the formula (VII) may be achieved, for example, by treating the benzoic acid derivative with DPPA (diphenoxy phosphoryl azide) in the presence of an inert amine such as triethylamine at a temperature range of room temperature to ca. 150° C. in an inert solvent such as benzene, toluene or xylene. Method B-2 comprises the preparation of the compound (I) of the invention wherein X is oxygen atom by converting a benzoic acid derivative of the formula (VIII) into a phenyl isocyanate derivative of the formula (IX) and reacting the isocyanate derivative with an aniline derivative of the formula (II) in an similar manner to Method B-1.

According to Method C-1, an aniline derivative of the formula (II) is treated with an activated derivative of carbonic acid such as phosgene or phenyl chloroformate to give a reactive intermediate of the formula (X) such as an arylcarbamyl chloride or an aryl ester of arylcarbamic acid, followed by reacting the intermediate with an aniline derivative of the formula (IV) at a temperature range of 0° C. to ca. 100° C. in the presence of an inert organic amine such as triethylamine or N,N-dimethylaniline in an inert solvent such as benzene, toluene, THF, chloroform or methylene chloride to obtain the compound (I) of the invention wherein X is oxygen atom. Method C-2 comprises the preparation of the compound (I) of the invention wherein X is oxygen atom by converting an aniline derivative of the formula (IV) into a reactive intermediate of the formula (XI) and reacting the resulting intermediate with an aniline derivative of the formula (II) in an similar manner to Method C-1.

According to Method D-1, an aniline derivative of the formula (II) is converted using different procedures to a reactive intermediate of the formula (XII), i.e., an alkyl thioester of arylthiocarbamic acid, followed by reacting the intermediate with an aniline derivative of the formula (IV) at a temperature range of 50° C. to boiling temperature of the solvent used in an inert solvent such as benzene, toluene or xylene to obtain the compound (I) of the invention wherein X is sulfur atom. Method D-2 comprises the preparation of the compound (I) of the invention wherein X is sulfur atom by converting an aniline derivative of the formula (IV) into a reactive intermediate of the formula (XIII), i.e., an alkyl thioester of arylthiocarbamic acid, and reacting the resulting intermediate with an aniline derivative of the formula (II) in an similar manner to Method D-1.

The compound (I) of the invention prepared according to any of the above methods can be purified by recrystallization from hexane, heptane, chloroform or methanol, or column chromatography over silica gel after concentrating the liquid part of the reaction mixture.

The present invention also provides an acyl coenzyme cholesterol acyltransferase inhibitor comprising a diphenylurea derivative as defined hereinbefore as active ingredient. The inhibitor may be administrated, preferably, orally to a human patient.

The present invention further provides a pharmaceutical composition for treating hyperlipemia and atherosclerosis comprising a therapeutically effective amount of a diphenylurea derivative as defined hereinbefore, in admixture with a pharmaceutically acceptable carrier, diluent or a mixture thereof. The composition may be administrated, preferably, orally to a patient.

The formulation for the oral administration may be tablet, granule, powder, capsule, etc. The inhibitor or pharmaceutical composition may further include usual additives known in the art, for example, an excipient such as glucose, lactose, corn starch or mannitol, a binder such as hydroxypropyl cellulose (HPC) and carboxymethyl cellulose (CMC), a disintegrating agent such as starch or powdery gelatin, a lubricating agent such as talc or magnesium stearate.

The dose of the compound according to the present invention, in the case of oral administration, is from 1 mg to 1000 mg per day for an adult, which may vary depending on the age, health conditions, body weight of the patient, as well as, if present, the type, frequency and desired effects of co-treatment.

EXAMPLES

The present invention is further illustrated in detail with reference to the following examples. It should be understood that the present invention is not limited solely to those examples.

EXAMPLE 1

Preparation of
1-(4-octylphenyl)-3-(2,6-dichlorophenyl)urea
(Compound No. 2 in Table 3)

To 10.6 ml (5.3 mmol) of a toluene solution of 0.50M 2,6-dichlorophenyl isocyanate was added 1.21 ml (5.32 mmol) of 4-octylaniline at room temperature and the whole was stirred for 16 hours. After removal of the solvent under reduced pressure, the residue was recrystallized from methanol to give 1.42 g (68% yield) of 1-(4-octylphenyl)-3-(2,6-dichlorophenyl)urea, the physical properties of which being shown in the following Table 3. The compounds No. 1, No. 13, No. 14, No. 17, and No. 18 listed in Table 3 were similarly prepared as above.

EXAMPLE 2

Preparation of
1-(4-nonylphenyl)-3-(2,6-diisopropylphenyl)urea
(Compound No. 19 in Table 3)

To a 10 ml toluene solution of 1.0 g (4.04 mmol) of 4-nonylbenzoic acid was added 0.66 ml (4.28 mmol) of triethylamine. After stirring at room temperature for 15 minutes, 0.89 ml (4.12 mmol) of DPPA (diphenoxy phosphoryl azide) was added to the mixture. The whole was heated for 2 hours under reflux and then cooled to room temperature. After the addition of 0.77 ml (4.08 mmol) of 2,6-diisopropylaniline, the reaction mixture was stirred for 16 hours and then concentrated. The residue was purified by subjecting it to column chromatography over silica gel (eluent: n-hexane/chloroform=1/1) to give 1.07 g (62% yield) of 1-(4-nonylphenyl)-3-(2,6-diisopropylphenyl)urea, the physical properties of which being shown in the following Table 3. The compounds No. 5, No. 6, No. 7, No. 8, No. 9, No. 10, No. 12, No. 16, No. 20, No. 21, No. 22, No. 23, and No. 26 listed in Table 3 were similarly prepared as above.

EXAMPLE 3

Preparation of
1-(4-octylphenyl)-3-(2,4,6-trichlorophenyl)urea
(Compound No. 3 in Table 3)

A 10 ml methylene chloride solution of 1.0 g (5.09 mmol) of 2,4,6-trichloroaniline was added dropwise over 2 minutes to a 10 ml methylene chloride solution of 0.6 ml (4.97 mmol) of trichloromethyl chloroformate cooled to 5°-6° C. After stirring at 5°-6° C. for 2 hours, the mixture was added with 1.04 g (5.06 mmol) of 4-octylaniline and then stirred at room temperature for 16 hours. The reaction mixture was extracted with chloroform, and washed with an aqueous saturated solution of sodium hydrogen carbonate and an aqueous saturated solution of sodium chloride, successively. The organic layer was dried over anhydrous magnesium sulfate. After the removal of the solvent under reduced pressure, the residue was recrystallized from a mixed solvent of n-heptane and chloroform to give 0.95 g (43% yield) of 1-(4-octylphenyl)-3-(2,4,6-trichlorophenyl)urea, the physical properties of which being shown in the following Table 3. The compounds No. 4 and No. 11 listed in Table 3 were similarly prepared as above.

EXAMPLE 4

Preparation of
1-(4-octylphenyl)-3-(2,6-diisopropylphenyl)thiourea
(Compound No. 15 in Table 3)

To a 10 ml N,N-dimethylformamide solution of 1.0 g (4.87 mmol) of 4-octylaniline was added 1.07 g (4.88 mmol) of 2,6-diisopropyl thioisocyanate, and the whole was stirred at 100° C. for 20 hours. The reaction mixture was extracted with ethyl acetate, washed with an aqueous solution of sodium chloride. The organic layer was dried over anhydrous magnesium sulfate and concentrated under reduced pressure. The residue was purified by subjecting it to column chromatography over silica gel (eluent: ethyl acetate/n-hexane=3/97) to give 0.96 g (46% yield) of 1-(4-octylphenyl)-3-(2,6-diisopropylphenyl)thiourea. The physical properties of the compound are shown in the following Table 3.

EXAMPLE 5

Preparation of
1-(2-hexylphenyl)-3-(2,6-diisopropylphenyl)urea
(Compound No. 24 in Table 3)

To a 5 ml n-hexane solution of 0.42 g (2.35 mmol) of 2-hexylaniline was added 5 ml (2.35 mmol) of a hexane solution of 0.47M 2,6-diisopropylphenyl isocyanate at room temperature and the whole was stirred for 16 hours. The precipitated crystals were collected by filtration to give 0.55 g (61% yield) of 1-(2-hexylphenyl)-3-(2,6-diisopropylphenyl)urea, the physical properties of which being shown in the following Table 3. The compound No. 25 listed in Table 3 was similarly prepared as above.

TABLE 3

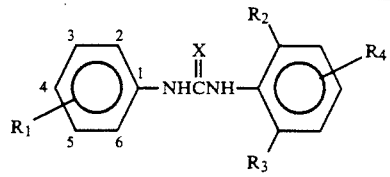

| Compound No. | $R_1$ | $R_2$ | $R_3$ | $R_4$ | X | IR (KBr) (cm$^{-1}$) | NMR (CDCl$_3$) ($\delta$) | Melting point (°C.) |
|---|---|---|---|---|---|---|---|---|
| 1 | 4-C$_8$H$_{17}$ | —F | —F | —H | O | 3340, 1645, 1595 1540 | 0.88(3H, t), 1.29(10H, m), 1.57(2H, m) 2.55(2H, t), 6.35(1H, bs), 6.81(1H, bs) 6.91(2H, m), 7.10(3H, m), 7.22(2H, m) | 173–175 |
| 2 | 4-C$_8$H$_{17}$ | —Cl | —Cl | —H | O | 3340, 1645, 1595 1540 | 0.88(3H, t), 1.29(10H, m), 1.57(2H, m) 2.55(2H, t), 6.35(1H, bs), 6.81(1H, bs) 6.96(2H, m), 7.10(3H, m), 7.22(2H, m) | 170–172 |
| 3 | 4-C$_8$H$_{17}$ | —Cl | —Cl | -4-Cl | O | 3370, 3330, 2950 1655, 1610, 1575 1550 | 0.88(3H, t), 1.27(10H, m), 1.51(2H, m) 2.45(2H, t), 6.81(2H, d), 7.00(2H, d) 7.13(2H, s), 7.21(1H, s), 7.52(1H, s) | 192–193 |
| 4 | 4-C$_8$H$_{17}$ | —Br | —Br | —H | O | 3300, 2940, 1640 1600, 1550 | 0.87(3H, t), 1.27(10H, m), 1.63(2H, m) 2.52(2H, t), 6.72(1H, s), 6.90(1H, t) 6.99(1H, m), 7.07(2H, d), 7.24(2H, d) 7.49(2H, d) | 181–183 |
| 5 | 4-C$_8$H$_{17}$ | —CH$_3$ | —CH$_3$ | —H | O | 3310, 2940, 1635 1595, 1545 | 0.87(3H, t), 1.26(10H, m), 1.58(2H, m) 2.33(6H, s), 2.53(2H, t), 5.98(1H, bs) 6.09(1H, bs), 7.09(2H, d), 7.20(5H, m) | 164–165 |
| 6 | 4-C$_8$H$_{17}$ | —CH$_3$ | —CH$_3$ | -4-CH$_3$ | O | 3310, 2925, 1640 1600, 1550 | 0.87(3H, t), 1.26(10H, m), 1.55(2H, m) 2.29(6H, s), 2.31(3H, s), 2.53(2H, t) 5.77(1H, bs), 6.08(1H, bs), 6.96(2H, s) 7.09(2H, s), 7.23(3H, m) | 165–167 |
| 7 | 4-C$_8$H$_{17}$ | —CH$_2$CH$_3$ | —CH$_2$CH$_3$ | —H | O | 3320, 2940, 1644 1600, 1558, 1507 | 0.87(3H, t), 1.23(16H, m), 1.55(2H, bs) 2.52(2H, t), 3.35(2H, bt), 6.10(2H, bs) 7.21(7H, m) | 125–127 |
| 8 | 4-C$_8$H$_{17}$ | —CH(CH$_3$)$_2$ | —CH(CH$_3$)$_2$ | —H | O | 3450, 3320, 2940 1647, 1605, 1559 1520 | 0.87(3H, t), 1.23(22H, m), 1.54(2H, m) 2.52(2H, t), 3.35(2H, bt), 6.10(2H, bs) 7.21(7H, m) | 120–122 |
| 9 | 4-C$_8$H$_{17}$ | —CH(CH$_3$)CH$_2$CH$_3$ | —CH$_2$CH$_3$ | —H | O | 3310, 2925, 1640 1600, 1540 | 0.87(6H, m), 1.25(16H, m), 1.55(4H, m) 2.53(2H, t), 2.74(2H, m), 3.11(1H, m) 5.82(1H, bs), 5.99(1H, bs), 7.08(2H, d) 7.20(4H, m), 7.34(1H, m) | 104–107 |
| 10 | 4-C$_8$H$_{17}$ | —CH$_3$ | —C(CH$_3$)$_3$ | —H | O | 3300, 2930, 1640 1600, 1540 | 0.87(3H, t), 1.26(10H, m), 1.43(9H, s) 1.65(2H, m), 2.35(3H, s), 2.52(2H, t) 6.00(2H, bs), 7.08(2H, d), 7.20(4H, m) 7.37(1H, m) | 189–191 |
| 11 | 4-C$_8$H$_{17}$ | —Cl | —Cl | -3-CH$_3$ | O | 3300, 2930, 1650 1600, 1550 | 0.88(3H, t), 1.27(10H, m), 1.61(2H, m) 2.30(3H, s), 2.52(2H, t), 6.64(1H, s) 6.93(1H, s), 7.12(3H, m), 7.24(3H, m) | 150–152 |
| 12 | 4-C$_8$H$_{17}$ | —OCH$_3$ | —OCH$_3$ | —H | O | 3310, 2945, 1640 1595, 1550 | 0.87(3H, t), 1.26(10H, m), 1.59(2H, m) 2.54(2H, t), 3.88(6H, m), 6.63(1H, bs) 6.63(2H, d), 6.90(1H, bs), 7.20(2H, d) 7.26(3H, m) | 149–150 |
| 13 | -2-C$_8$H$_{17}$ | —CH(CH$_3$)$_2$ | —CH(CH$_3$)$_2$ | —H | O | 3300, 2950, 1630 1580, 1540 | (DMSO-d$_6$), 0.85(3H, t), 1.13(6H, s) 1.15(6H, s), 1.25(10H, m), 1.55(2H, m) 2.61(2H, t), 3.20(2H, m), 6.94(1H, t) 7.13(5H, m), 7.61(1H, d), 7.94(2H, d) | 175–176 |
| 14 | -3-C$_8$H$_{17}$ | —CH(CH$_3$)$_2$ | —CH(CH$_3$)$_2$ | —H | O | 3310, 2930, 1640 1560 | 0.87(3H, t), 1.25(22H, m), 1.57(2H, m) 2.54(2H, t), 3.35(2H, m), 5.96(1H, bs) 6.85(1H, bs), 7.07(1H, d), 7.10(3H, m) 7.25(2H, m), 7.37(1H, m) | 92–94 |
| 15 | 4-C$_8$H$_{17}$ | —CH(CH$_3$)$_2$ | —CH(CH$_3$)$_2$ | —H | S | 3360, 3140, 2950 2920, 2850, 1530 1485, 1460, 1330 1260, 1210 | 0.87(3H, t), 1.25(22H, m), 1.56(2H, m) 2.55(2H, t), 3.30(2H, m), 6.87(1H, s) 7.19(7H, m), 8.26(1H, s) | oil |
| 16 | 4-C$_5$H$_{11}$ | —CH(CH$_3$)$_2$ | —CH(CH$_3$)$_2$ | —H | O | 3460, 3325, 2940 1645, 1600, 1558 | 0.87(3H, t), 1.25(16H, m), 1.55(2H, m) 2.52(2H, t), 3.36(2H, m), 7.21(7H, m) | 230–231 |
| 17 | 4-C$_6$H$_{13}$ | —CH(CH$_3$)$_2$ | —CH(CH$_3$)$_2$ | —H | O | 3450, 3320, 2940 1644, 1605, 1558 1520 | 0.86(3H, t), 1.23(18H, m), 1.54(2H, bt) 2.52(2H, t), 3.35(2H, bt), 6.19(2H, bs) 7.20(7H, m) | 190–192 |
| 18 | 4-C$_7$H$_{15}$ | —CH(CH$_3$)$_2$ | —CH(CH$_3$)$_2$ | —H | O | 3440, 3330, 2940 1648, 1605, 1558 1520 | 0.87(3H, t), 1.22(20H, m), 1.54(2H, bt) 2.51(2H, t), 3.35(2H, bt), 6.42(2H, bs) 7.19(7H, m) | 142–143 |
| 19 | 4-C$_9$H$_{19}$ | —CH(CH$_3$)$_2$ | —CH(CH$_3$)$_2$ | —H | O | 3320, 2950, | 0.87(3H, t), 1.20(24H, m), 1.57(2H, m) | 106– |

TABLE 3-continued

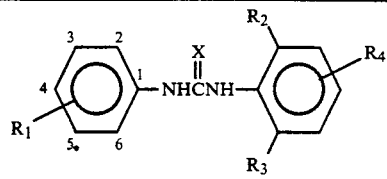

| Compound No. | $R_1$ | $R_2$ | $R_3$ | $R_4$ | X | IR (KBr) (cm$^{-1}$) | NMR (CDCl$_3$) ($\delta$) | Melting point (°C.) |
|---|---|---|---|---|---|---|---|---|
| | | | | | | 1640 1600, 1555 | 2.52(2H, t), 3.53(2H, m), 5.87(1H, s) 6.01(1H, bs), 7.08(2H, d), 7.16(4H, m) 7.36(1H, m) | 108 |
| 20 | 4-$C_{10}H_{21}$ | —CH(CH$_3$)$_2$ | —CH(CH$_3$)$_2$ | —H | O | 3330, 2945, 1640 1600, 1555 | 0.87(3H, t), 1.24(26H, m), 1.62(2H, m) 2.52(2H, t), 3.53(2H, m), 6.05(2H, bs) 7.04(2H, d), 7.19(2H, d), 7.26(2H, d) 7.36(1H, m) | 90–92 |
| 21 | 4-$C_{12}H_{25}$ | —CH(CH$_3$)$_2$ | —CH(CH$_3$)$_2$ | —H | O | 3330, 2950, 1640 1600, 1560 | 0.87(3H, t), 1.25(30H, m), 1.58(2H, m) 2.52(2H, t), 3.37(2H, m), 6.05(2H, bs) 7.06(2H, d), 7.20(2H, d), 7.39(1H, m) | 89–90 |
| 22 | 4-$C_{15}H_{31}$ | —CH(CH$_3$)$_2$ | —CH(CH$_3$)$_2$ | —H | O | 3330, 2940, 1640 1600, 1555 | 0.88(3H, t), 1.25(36H, m), 1.57(2H, m) 2.52(2H, t), 3.35(2H, m), 5.87(1H, s) 6.01(1H, bs), 7.05(2H, d), 7.20(2H, d) 7.26(2H, d), 7.38(1H, m) | 91–93 |
| 23 | 4-$C_{18}H_{37}$ | —CH(CH$_3$)$_2$ | —CH(CH$_3$)$_2$ | —H | O | 3310, 2930, 1640 1600, 1560 | 0.86(3H, t), 1.25(42H, m), 1.54(2H, m) 2.52(2H, t), 3.35(2H, m), 6.10(2H, bs) 7.04(2H, d), 7.19(2H, d), 7.26(2H, d) 7.35(1H, m) | 97–98.5 |
| 24 | 2-$C_6H_{13}$ | —CH(CH$_3$)$_2$ | —CH(CH$_3$)$_2$ | —H | O | 3320, 2940, 1640 1540 | 0.86(3H, t), 1.22(20H, m), 2.13(2H, bs) 3.38(2H, bs), 6.05(1H, bs), 6.18(1H, bs) 7.03(2H, bs), 7.24(4H, m), 7.34(1H, m) | 189–191 |
| 25 | 3-$C_6H_{13}$ | —CH(CH$_3$)$_2$ | —CH(CH$_3$)$_2$ | —H | O | 3300, 2960, 1640 1610, 1560 | 0.86(3H, t), 1.26(18H, m), 1.57(2H, m) 2.52(2H, t), 3.35(2H, m), 5.96(2H, bs) 6.86(1H, d), 7.10(3H, m), 7.26(2H, m) 7.39(1H, t) | 129–131 |
| 26* | 4-C(CH$_3$)$_3$ | —CH(CH$_3$)$_2$ | —CH(CH$_3$)$_2$ | —H | O | 3440, 3320, 2955 1644, 1602, 1550 | 1.28(21H, m), 3.35(2H, m), 6.12(2H, bs) 7.28(7H, m) | |

*Comparative Example

TEST EXAMPLE 1

The effect of reducing a lipid level in blood by the action of the compounds according to the present invention was determined as follows:

Male golden Syrian hamsters weighing from 80 to 100 g were randomly divided into groups. The hamsters were first fed standard laboratory diets (solid feed MF-1 for mouse/rat/hamster, manufactured by Oriental Yeast Industries, KK) for 3 days. Then, they were fed the experimental diet containing 1% cholesterol and 0.5% cholic acid (manufactured by Oriental Yeast Industries, KK), ad libitum. At the same time, the compounds of the invention formulated in a shown dose (25 mg or 50 mg/10 ml water/kg) were administrated to the animals orally once a day at a determined time for 5 days. Water was administrated orally to the hamsters of control group in an amount of 10 ml per 1 kg of body weight. After five days of administrating the compounds, they were anesthetized with Pentobarbital Na (Nembutal injection, manufactured by Dainabbot) and three hours after the final administration of the test compound, a blood samples (2–3 ml) was taken from abdominal cava. The serum was separated by centrifuging.

The cholesterol level in the serum was determined by using a blood cholesterol measuring kit, Determina-TC5 manufactured by Kyowa Medix Co. The results are represented by percent inhibition (%) of cholesterol level in serum relative to that of the control group, and shown in the following Table 4, each compound number corresponding to that in the above Table 3.

TABLE 4

| Compound No. | Percent inhibition of cholesterol in serum (%) | |
|---|---|---|
| | 25 mg/kg | 5 mg/kg |
| 2 | 49 | |
| 4 | 55 | |
| 5 | 44 | |
| 7 | 48 | |
| 8 | 55 | 35 |
| 11 | 47 | |
| 12 | 54 | |
| 13 | 54 | |
| 16 | 34 | |
| 17 | 60 | |
| 18 | 49 | |
| 19 | 64 | |
| 20 | 59 | |
| 26[1)] | 19 | |

[1)]Compound No. 26 was used as a reference.

TEST EXAMPLE 2

The ACAT inhibitory action of the compounds according to the present invention was measured as follows:

ACAT activity in the hamster microsomes was determined by measuring the rate of radio-active cholesteryl-[$^{14}$C] oleate formation from cholesterol and radio-labelled oleoyl coenzyme A ($^{14}$C) with or without test compound.

Calculations of $IC_{50}$ value were made using data of the percent inhibition at each compound concentration. The results are shown in the following Table 5, each compound number corresponding to that in Table 3.

TABLE 5

| Compound No. | ACAT inhibitory activity $IC_{50}$ ($\mu M$) |
| --- | --- |
| 8 | 0.004 |
| 17 | 0.011 |
| 18 | 0.006 |
| 19 | 0.010 |
| 20 | 0.012 |

TEST EXAMPLE 3

Acute toxicity test

A compound according to the present invention suspended in a 1% tragacanth solution was administrated orally to SD male and female rats. Then, the number of fatal rats was counted during seven day observation. The $LD_{50}$ value is shown in the following Table 6, the compound number corresponding to that in the above Table 3.

TABLE 6

| Compound No. | $LD_{50}$ (mg/kg P.O.) |
| --- | --- |
| 8 | >2000 |

EXAMPLES OF FORMULATION (1) Tablet

The following ingredients were mixed according to the usual manner and compressed to a tablet using a conventional machine.

| | |
| --- | --- |
| Compound No. 8 | 10 mg |
| Crystalline cellulose | 21 mg |
| Corn starch | 33 mg |
| Lactose | 65 mg |
| Magnesium stearate | 1.3 mg |

(2) Soft capsule

The following ingredients were mixed according to the usual manner and packed into a soft capsule.

| | |
| --- | --- |
| Compound No. 8 | 10 mg |
| Olive oil | 105 mg |
| Lecithine | 6.5 mg |

What is claimed is:

1. A diphenylurea derivative represented by the following formula (I):

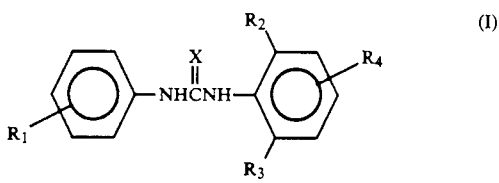

wherein $R_1$ is an alkyl group of 5 to 18 carbon atoms, each of $R_2$ and $R_3$ is independently an alkyl group of 1 to 5 carbon atoms, an alkoxy group of 1 to 5 carbon atoms or a halogen atom, $R_4$ is hydrogen atom, an alkyl group of 1 to 5 carbon atoms, an alkoxy group of 1 to 5 carbon atoms or a halogen atom, and X is oxygen atom or sulfur atom.

2. A diphenylurea derivative as defined in claim 1, wherein $R_1$ is a normal alkyl group of 6 to 10 carbon atoms.

3. A diphenylurea derivative as defined in claim 2, wherein $R_1$ is present at 2- or 4-position.

4. A diphenylurea derivative as defined in claim 3, wherein $R_4$ is hydrogen atom.

5. A pharmaceutical composition for treating hyperlipemia and atherosclerosis comprising a therapeutically effective amount of a diphenylurea derivative as defined in claim 1, in admixture with a pharmaceutically acceptable carrier, diluent, or a mixture thereof.

* * * * *